US00PP11042P

United States Patent [19]

Dümmen

[11] Patent Number: Plant 11,042

[45] Date of Patent: Aug. 24, 1999

[54] POINSETTIA PLANT NAMED 'DUESPOTPINK'

[75] Inventor: Marga Dümmen, Rheinberg, Germany

[73] Assignee: Dümmen Jungpflanzenkulturen, Rheinberg, Germany

[21] Appl. No.: 09/019,035

[22] Filed: Feb. 5, 1998

[51] Int. Cl.[6] ..... A01H 5/00

[52] U.S. Cl. ..... Plt./306

[58] Field of Search ..... Plt./306, 307

[56] References Cited

U.S. PATENT DOCUMENTS

P.P. 10,182 1/1998 Zerr ..... Plt./306

*Primary Examiner*—Howard J. Locker
*Assistant Examiner*—Kent L. Bell
*Attorney, Agent, or Firm*—C. A. Whealy

[57] ABSTRACT

A new and distinct cultivar of Poinsettia plant named 'Duespotpink', characterized by its dark pink bracts; freely branching plant habit; compact plant habit; and exceptional postproduction longevity.

1 Drawing Sheet

BACKGROUND OF THE INVENTION

The present invention relates to a new and distinct cultivar of Poinsettia plant, botanically known as *Euphorbia pulcherrima* Willd., and hereinafter referred to by the cultivar name 'Duespotpink'. The new cultivar is being marketed under the name 'Spotlight Pink'.

The new cultivar is a product of a planned breeding program conducted by the inventor in Rheinberg, Germany. The objective of the breeding program was to develop freely branching poinsettia varieties with excellent postproduction longevity.

The new cultivar is a naturally-occurring mutation of the commercial cultivar 'HWD Spotlight', disclosed in U.S. Plant Pat. No. 9,854. The new cultivar was discovered and selected by the inventor 1995 in a controlled environment in Rheinberg, Germany, as a single flowering plant among a population of plants of the parent cultivar 'HWD Spotlight'. The new cultivar consistently formed inflorescences with pink bracts compared to the red-colored bracts of plants of the cultivar 'HWD Spotlight'.

Asexual reproduction of the new cultivar by terminal cuttings taken at Rheinberg, Germany, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Duespotpink'. These characteristics in combination distinguish 'Duespotpink' as a new and distinct cultivar:

1. Dark pink bracts.

2. Compact and freely branching plant habit.

3. Excellent postproduction longevity.

The new cultivar can be compared to the commercial cultivar '490 Pink' (U.S. Plant Pat. No. 8,817). However in side-by-side comparisons conducted by the inventor in Rheinberg, Germany, the new cultivar differs from plants of the cultivar '490 Pink' in the following characteristics:

1. Plants of the new cultivar are more vigorous than plants of the cultivar '490 Pink'.

2. Plants of the new cultivar flower about one week later than plants of the cultivar '490 Pink'.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a typical plant of 'Duespotpink', pinched, planted in a 15-cm container.

DETAILED BOTANICAL DESCRIPTION

The cultivar 'Duespotpink' has not been observed under all possible environmental conditions. The phenotype may vary somewhat with variations in environment such as temperature, daylength and light intensity, without, however, any variance in genotype. The following observations and measurements describe plants grown in Astabula, Ohio, under commercial practice in a polyethylene-covered greenhouse with day temperatures about 22 to 26° C., night temperatures about 20 to 22° C. and light levels about 30 to 50 klux. Plants were grown in 15-cm pots, pinched one time, and flowered under naturally-occurring long nyctoperiods. One spray application of the growth retardant combination, daminozide (1000 ppm) and chlormequat chloride (2000 ppm), was applied to the plants two weeks after pinching.

In the following description, color references are made to The Royal Horticultural Society Colour Chart except where general terms of ordinary dictionary significance are used.

Botanical classification: *Euphorbia pulcherrima* Willd. cultivar 'Duespotpink'.

Parentage: Naturally-occurring mutation of commercial cultivar 'HWD Spotlight', disclosed in U.S. Plant Pat. No. 9,854.

Propagation:

*Type cutting.*—Terminal cuttings.

*Time to initiate roots.*—Summer: About 8 days at 22° C. Winter: About 10 days at 22° C.

*Time to develop roots.*—Summer: About 21 days at 20° C. Winter: About 26 days at 20° C.

*Rooting habit.*—Fine, freely branching.

Plant description:

*Plant form.*—Inverted triangle, top of plant rounded to flat.

*Growth habit.*—Freely branching and upright. Branching is enhanced by the removal of the apical shoot tip, typically about eight lateral branches develop after pinching. Moderate growth rate and moderately vigorous. Relatively compact, suitable for 6 to 16-cm containers, most appropriate for 12.5 to 15-cm containers.

*Plant height.*—About 19.5 cm.

*Stem description.*—Lateral branch length: About 11.5 cm. Internode length: About 2.1 cm. Color: Closest to 146B.

*Crop time.*—From unrooted cuttings to a flowering plant in a 15-cm container, about 15 weeks are required.

*Foliage description.*—Arrangement: Opposite. Quantity of leaves: Usually 40 to 56 per flowering plant. Length: About 10 cm. Width: About 6 cm. Shape: Ovate, lobed, fiddle-shaped. Apex: Acuminate. Base: Obtuse. Margin: Entire, moderately pinnately lobed. Texture: Dull, leathery, glabrous. Color: Young foliage, upper surface: Darker than 137A. Young foliage, lower surface: 137C. Mature foliage, upper surface: Darker than 139A. Mature foliage, lower surface: 137A. Venation, upper surface: 145A. Venation, lower surface: 145C. Petiole: Length: About 5.25 cm. Diameter: About 2.25 mm. Color: 145C.

Inflorescence description:

*Inforescence type and habit.*—Inflorescences are compound corymbs of cyathia with colored flower bracts subtending the cyathia.

*Natural flowering season.*—Autumn/winter in Northern Hemisphere. Flower initiation and development can be induced under long nyctoperiod conditons.

*Time to flower.*—About 8.5 weeks under long nyctoperiod conditions.

*Quantity of inflorescences.*—One per lateral branch, usually about 8 per plant.

*Quantity of cyathia.*—About 10 to 15 per corymb.

*Inflorescence size.*—Diameter: About 28 cm. Height (depth): About 4.5 cm.

*Flower bracts.*—Attitude: Perpendicular to slightly angled upward with respect to stem axis. Quantity of flower bracts: About 14 per inflorescence. Length: Upper, smaller bracts: About 6.6 cm. Lower, larger bracts: About 11.5 cm. Width: Upper, smaller bracts: About 3.8 cm. Lower, larger bracts: About 8.75 cm. Shape: Upper, smaller bracts: Ovate, not lobed. Lower, larger bracts: Ovate, lobed. Apex: Acute. Base: Obtuse. Margin: Entire, larger bracts lobed. Texture: Smooth to slightly rugose. Color: When opening, upper: 53D. Mature, upper surface: 51A. Mature, lower surface: 51B. Fading to: 51B/51C. After senescence: 51C. Peduncle: Length: About 3 mm. Aspect: Erect. Color: 146B.

*Cyathia.*—Quantity: Usually about 10 to 15 per corymb. Diameter of cyathia cluster: About 2 cm. Color: 144A. Stamens: Stamen number: 20 to 30 per cyathium. Anther size: About 0.5 mm. Anther shape: Rounded. Pistils: Pistil number: 1 per cyathium. Stigma shape: Trilobate. Style length: About 2 mm. Nectaries: Usually one and sometimes two per cyathium.

Disease resistance: No fungal, bacterial nor viral problems observed on plants grown under commercial conditions.

Postproduction longevity: Generally plants maintain good substance and bract color for about five to six weeks under interior conditions.

It is claimed:

1. A new and distinct cultivar of Poinsettia plant named 'Duespotpink', as illustrated and described.

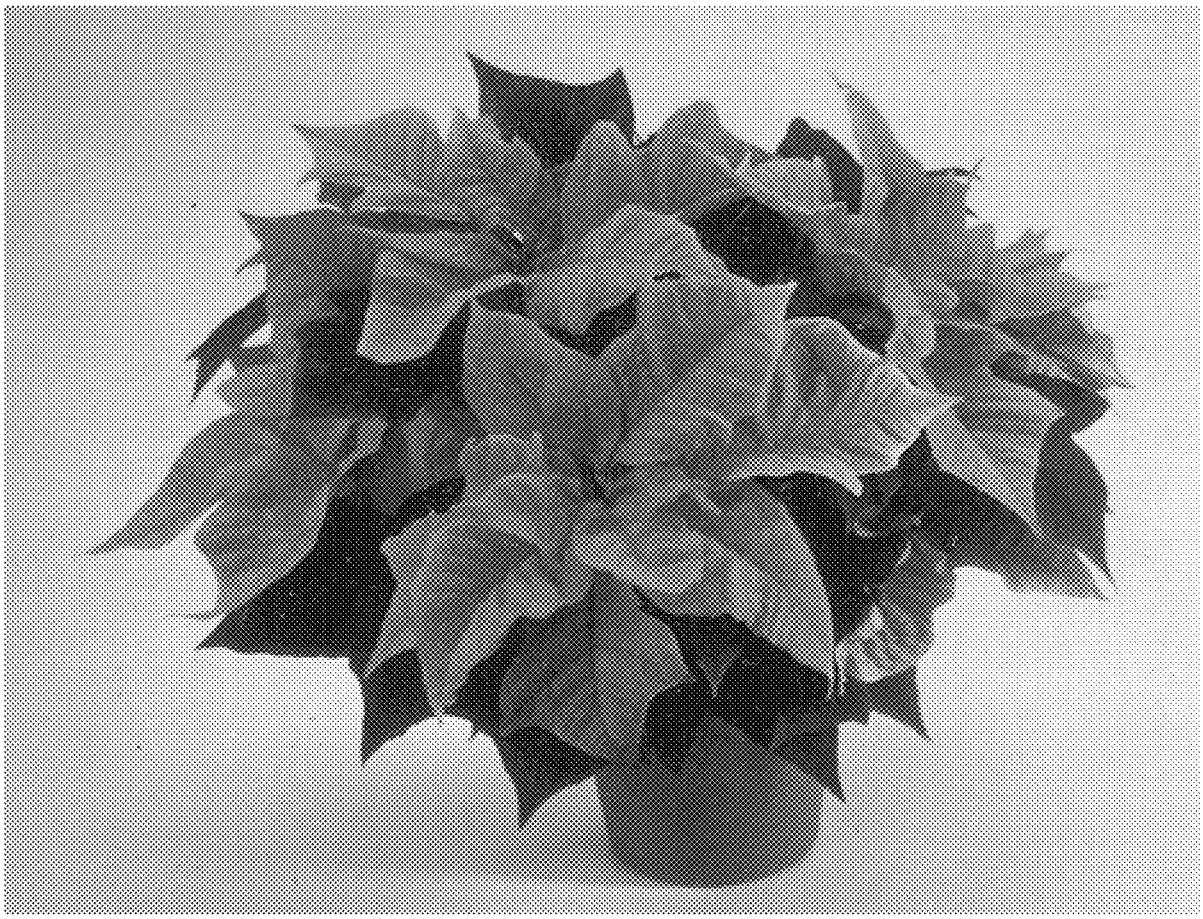

* * * * *